United States Patent
Grandfield et al.

(10) Patent No.: US 8,795,317 B2
(45) Date of Patent: Aug. 5, 2014

(54) EMBOLIC OBSTRUCTION RETRIEVAL DEVICES AND METHODS

(75) Inventors: Ryan M. Grandfield, Livermore, CA (US); Scott D. Wilson, Redwood City, CA (US); John H. Miller, Redwood City, CA (US); Emily Vu, San Jose, CA (US); Kirk L. Pedersen, San Francisco, CA (US); Craig L. Bonsignore, Pleasanton, CA (US); Elliot H. Sanders, Hilo, CA (US)

(73) Assignee: Concentric Medical, Inc., Fremont, CA (US)

( * ) Notice: Subject to any disclaimer, the term of this patent is extended or adjusted under 35 U.S.C. 154(b) by 54 days.

(21) Appl. No.: 12/499,713

(22) Filed: Jul. 8, 2009

(65) Prior Publication Data

US 2011/0009875 A1    Jan. 13, 2011

(51) Int. Cl.
  *A61F 2/01* (2006.01)
  *A61B 17/22* (2006.01)
(52) U.S. Cl.
  USPC ............................ 606/200; 606/127; 606/159
(58) Field of Classification Search
  USPC .................. 606/110, 113, 127, 128, 200, 159
  See application file for complete search history.

(56) References Cited

U.S. PATENT DOCUMENTS

| | | | |
|---|---|---|---|
| 4,347,846 A | 9/1982 | Dormia | |
| 4,706,671 A | 11/1987 | Weinrib | |
| 4,776,337 A | 10/1988 | Palmaz | |
| 4,886,062 A | 12/1989 | Wiktor | |
| 5,011,488 A | 4/1991 | Ginsburg | |
| 5,192,286 A | 3/1993 | Phan et al. | |
| 5,354,308 A | 10/1994 | Simon et al. | |
| 5,370,653 A | 12/1994 | Cragg | |
| 5,370,683 A | 12/1994 | Fontaine | |

(Continued)

FOREIGN PATENT DOCUMENTS

| AU | 2003254553 A1 | 2/2004 |
|---|---|---|
| CA | 2492978 A1 | 1/2004 |

(Continued)

OTHER PUBLICATIONS

Wilson, Scott et al., Devices and Methods for Temporarily Opening a Blood Vessel, U.S. Utility Patent Application, Oct. 31, 2008.

(Continued)

*Primary Examiner* — Kathleen Holwerda
(74) *Attorney, Agent, or Firm* — Tim L. Kitchen; Peter B. Scull; Hamilton, DeSanctis & Cha, LLP

(57) ABSTRACT

An embolic obstruction retrieval device including a self-expandable member having a proximal end portion, a main body portion and a distal end portion. Each of the self-expandable portions consists of a plurality of cell structures formed by intersecting strut members. At least one proximal cell structure in the proximal end portion has one or more struts that have a width and/or thickness greater than the width and/or thickness of the majority of strut members in the main body and distal end portions of the expandable member. Attached to at least one of the proximal-most cell structures in the proximal end portion is a proximally extending flexible wire having sufficient length and flexibility to navigate the tortuous vasculature and access the embolic obstruction. In one implementation, the embolic obstruction retrieval device is delivered to the embolic obstruction through the lumen of a delivery catheter.

9 Claims, 26 Drawing Sheets

(56) References Cited

U.S. PATENT DOCUMENTS

| | | | |
|---|---|---|---|
| 5,456,667 A | 10/1995 | Ham et al. |
| 5,496,365 A | 3/1996 | Sgro |
| 5,643,312 A | 7/1997 | Fischell et al. |
| 5,667,486 A | 9/1997 | Mikulich et al. |
| 5,681,335 A | 10/1997 | Serra et al. |
| 5,795,331 A | 8/1998 | Cragg et al. |
| 5,800,519 A | 9/1998 | Sandock |
| 5,800,520 A | 9/1998 | Fogarty et al. |
| 5,800,525 A | 9/1998 | Bachinski et al. |
| 5,810,872 A | 9/1998 | Kanesaka et al. |
| 5,827,321 A | 10/1998 | Roubin et al. |
| 5,836,966 A | 11/1998 | St. Germain |
| 5,843,117 A | 12/1998 | Alt et al. |
| 5,855,600 A | 1/1999 | Alt |
| 5,876,449 A | 3/1999 | Starck et al. |
| 5,879,370 A | 3/1999 | Fischell et al. |
| 5,895,398 A | 4/1999 | Wensel et al. |
| 5,895,406 A | 4/1999 | Gray et al. |
| 5,911,754 A | 6/1999 | Kanesaka et al. |
| 5,913,895 A | 6/1999 | Burpee et al. |
| 5,968,088 A | 10/1999 | Hansen et al. |
| 5,972,018 A | 10/1999 | Israel et al. |
| 5,984,929 A | 11/1999 | Bashiri et al. |
| 6,027,526 A | 2/2000 | Limon et al. |
| 6,030,397 A | 2/2000 | Monetti et al. |
| 6,042,597 A | 3/2000 | Kveen et al. |
| 6,059,822 A | 5/2000 | Kanesaka et al. |
| 6,066,149 A | 5/2000 | Samson et al. |
| 6,066,158 A | 5/2000 | Engelson et al. |
| 6,106,548 A | 8/2000 | Roubin et al. |
| 6,146,403 A | 11/2000 | St. Germain |
| 6,200,335 B1 | 3/2001 | Igaki |
| 6,206,911 B1 | 3/2001 | Milo |
| 6,217,608 B1 | 4/2001 | Penn et al. |
| 6,273,910 B1 | 8/2001 | Limon |
| 6,309,414 B1 | 10/2001 | Rolando et al. |
| 6,350,271 B1 | 2/2002 | Kurz et al. |
| 6,398,805 B1 | 6/2002 | Alt |
| 6,402,431 B1 | 6/2002 | Nish |
| 6,402,771 B1 | 6/2002 | Palmer et al. |
| 6,409,754 B1 | 6/2002 | Smith et al. |
| 6,423,091 B1 | 7/2002 | Hojeibane |
| 6,468,301 B1 | 10/2002 | Amplatz et al. |
| 6,475,236 B1 | 11/2002 | Roubin et al. |
| 6,478,816 B1 | 11/2002 | Kveen et al. |
| 6,482,217 B1 | 11/2002 | Pintor et al. |
| 6,488,703 B1 | 12/2002 | Kveen et al. |
| 6,491,719 B1 | 12/2002 | Fogarty et al. |
| 6,514,273 B1 | 2/2003 | Voss et al. |
| 6,551,342 B1* | 4/2003 | Shen et al. ............... 606/200 |
| 6,575,995 B1* | 6/2003 | Huter et al. ............... 606/200 |
| 6,641,590 B1 | 11/2003 | Palmer et al. |
| 6,660,021 B1 | 12/2003 | Palmer et al. |
| 6,679,893 B1 | 1/2004 | Tran |
| 6,692,504 B2 | 2/2004 | Kurz et al. |
| 6,706,054 B2 | 3/2004 | Wessman et al. |
| 6,716,240 B2 | 4/2004 | Fischell et al. |
| 6,818,013 B2 | 11/2004 | Mitelberg et al. |
| 6,818,613 B2 | 11/2004 | Sharma et al. |
| 6,881,222 B2 | 4/2005 | White et al. |
| 6,949,120 B2 | 9/2005 | Kveen et al. |
| 6,960,228 B2 | 11/2005 | Mitelberg et al. |
| 7,008,434 B2 | 3/2006 | Kurz et al. |
| 7,037,321 B2 | 5/2006 | Sachdeva et al. |
| 7,037,331 B2 | 5/2006 | Mitelberg et al. |
| 7,081,130 B2 | 7/2006 | Jang |
| 7,108,714 B1 | 9/2006 | Becker |
| 7,195,648 B2 | 3/2007 | Jones et al. |
| 7,291,166 B2 | 11/2007 | Cheng et al. |
| 7,300,458 B2 | 11/2007 | Henkes et al. |
| 7,311,726 B2 | 12/2007 | Mitelberg et al. |
| 7,316,692 B2* | 1/2008 | Huffmaster ............... 606/127 |
| 7,485,130 B2 | 2/2009 | St. Germain |
| 7,651,513 B2 | 1/2010 | Teoh et al. |
| 7,655,033 B2 | 2/2010 | Fearnot et al. |
| 7,678,119 B2 | 3/2010 | Little et al. |
| 7,811,300 B2 | 10/2010 | Feller, III et al. |
| 7,875,044 B2 | 1/2011 | Feller, III et al. |
| 7,887,560 B2 | 2/2011 | Kusleika |
| 2001/0047200 A1 | 11/2001 | White et al. |
| 2003/0004567 A1 | 1/2003 | Boyle et al. |
| 2003/0100917 A1 | 5/2003 | Boyle et al. |
| 2003/0116751 A1 | 6/2003 | Elman |
| 2003/0176914 A1 | 9/2003 | Rabkin et al. |
| 2003/0199921 A1 | 10/2003 | Palmer et al. |
| 2004/0068314 A1 | 4/2004 | Jones et al. |
| 2004/0199175 A1 | 10/2004 | Jaeger et al. |
| 2004/0236368 A1 | 11/2004 | McGuckin et al. |
| 2005/0209678 A1 | 9/2005 | Henkes et al. |
| 2005/0267491 A1 | 12/2005 | Kellett et al. |
| 2006/0116751 A1 | 6/2006 | Bayle et al. |
| 2006/0265048 A1 | 11/2006 | Cheng et al. |
| 2006/0287701 A1 | 12/2006 | Pal |
| 2007/0038178 A1 | 2/2007 | Kusleika |
| 2007/0191866 A1 | 8/2007 | Palmer et al. |
| 2007/0198051 A1 | 8/2007 | Clubb et al. |
| 2007/0225739 A1 | 9/2007 | Pintor et al. |
| 2007/0280367 A1 | 12/2007 | Nakao et al. |
| 2007/0288054 A1* | 12/2007 | Tanaka et al. ............... 606/200 |
| 2008/0125855 A1 | 5/2008 | Henkes et al. |
| 2008/0208244 A1 | 8/2008 | Boylan et al. |
| 2008/0262487 A1 | 10/2008 | Wensel et al. |
| 2009/0105722 A1 | 4/2009 | Fulkerson et al. |
| 2009/0105737 A1 | 4/2009 | Fulkerson et al. |
| 2010/0100106 A1 | 4/2010 | Ferrera |
| 2010/0114135 A1 | 5/2010 | Wilson et al. |
| 2010/0161034 A1 | 6/2010 | Leanna et al. |
| 2010/0174309 A1 | 7/2010 | Fulkerson et al. |
| 2010/0318097 A1 | 12/2010 | Ferrera et al. |
| 2010/0331853 A1 | 12/2010 | Garcia et al. |
| 2011/0009950 A1 | 1/2011 | Grandfield et al. |
| 2011/0130784 A1 | 6/2011 | Kusleika |
| 2011/0196414 A1 | 8/2011 | Porter et al. |
| 2012/0123466 A1 | 5/2012 | Porter et al. |

FOREIGN PATENT DOCUMENTS

| | | |
|---|---|---|
| DE | 4032759 A1 | 4/1992 |
| DE | 19834956 A1 | 5/1999 |
| DE | 10233085 A1 | 1/2004 |
| DE | 10301850 A1 | 1/2004 |
| DE | 10301850 A1 | 7/2004 |
| EP | 0897698 A2 | 2/1999 |
| EP | 0914807 A2 | 5/1999 |
| EP | 0916362 A1 | 5/1999 |
| EP | 1266640 A2 | 12/2002 |
| EP | 1362564 A1 | 11/2003 |
| EP | 1266640 A3 | 1/2004 |
| EP | 1266640 B1 | 8/2007 |
| EP | 1534178 B1 | 10/2007 |
| EP | 1351626 B1 | 2/2008 |
| EP | 1542617 A1 | 1/2011 |
| GB | 2463592 B | 8/2010 |
| JP | 62049841 A | 3/1987 |
| JP | 7124251 A | 5/1995 |
| JP | 2010264261 A | 11/2010 |
| WO | 9704711 A1 | 2/1997 |
| WO | 9725000 A1 | 7/1997 |
| WO | 0145592 A1 | 6/2001 |
| WO | WO0145592 A1 | 6/2001 |
| WO | 2004006804 A1 | 1/2004 |
| WO | 2004008991 A1 | 1/2004 |
| WO | WO2004008991 A | 1/2004 |
| WO | 2008063156 A2 | 5/2008 |
| WO | 2010010545 A1 | 1/2010 |

OTHER PUBLICATIONS

EV3, Fully Deployable. Completely Retrievable. Solitaire AB Neurovascular Remodeling Device, Solitaire AB Brochure, www.ev3.net, accessed on Jul. 16, 2009.

International Search Report and Written Opinion for PCT International Application No. PCT/US2010/041434 issued by the ISA dated Sep. 8, 2010, Virginia, US.

(56) References Cited

OTHER PUBLICATIONS

International Search Report and Written Opinion for PCT International Application No. PCT/US2010/041434 issued by the ISA dated Sep. 8, 2010.
PCT International Preliminary Report on Patentability for PCT International Application No. PCT/US2012/023858 issued Oct. 8, 2013, IB of WIPO, Geneva Switzerland, containing the written opinion of the US Patent Office for PCT/US2012/023858 issued Jun. 4, 2012.
PCT International Preliminary Report on Patentability for PCT/US2010/041434, issued Jan. 10, 2012, IB of WIPO, Geneva Switzerland, containing the written opinion of the US Patent Office for PCT/US2010/041434, issued Sep. 8, 2010, Alexandria, VA, USA.
International Search Report and Written Opinion for PCT International Application No. PCT/US2012/023858 issued by the ISA dated Jun. 4, 2012.
Extended and Supplementary European Search Report for PCT/US2012/023858 issued by the European Patent Office, Rijswijk, Netherlands dated Jan. 20, 2014.

\* cited by examiner

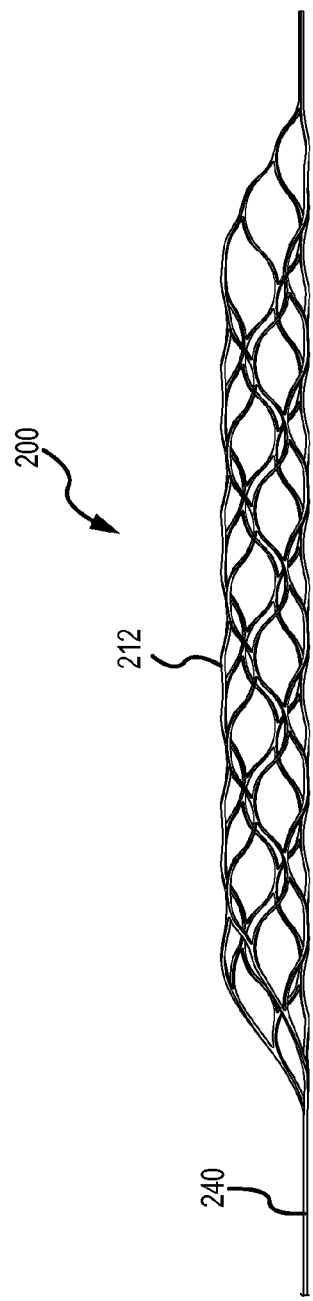

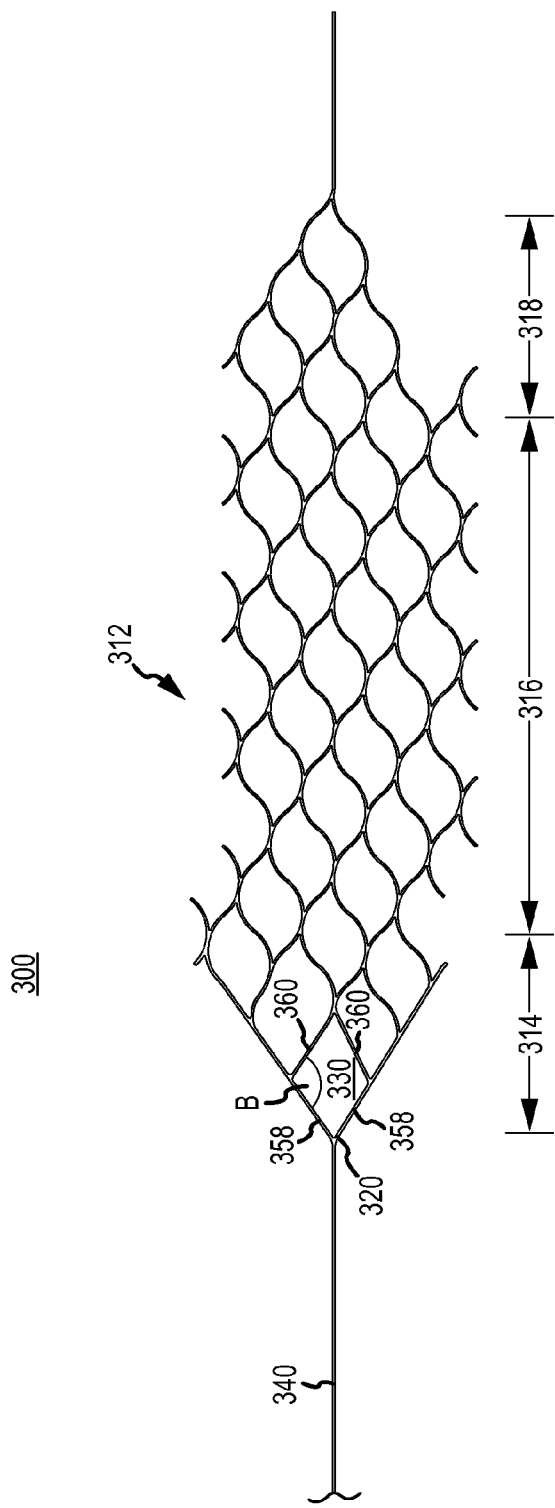

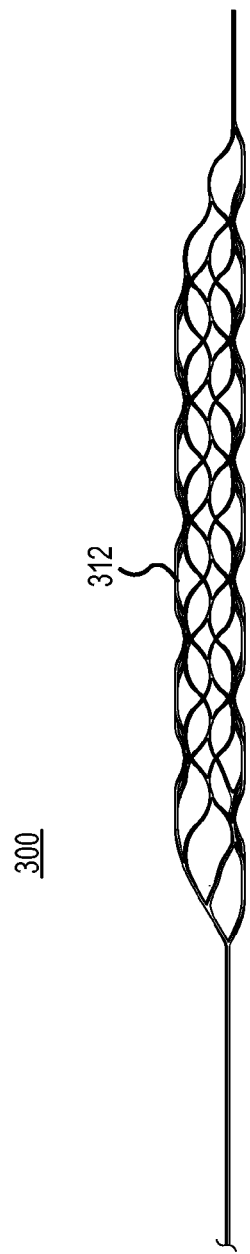

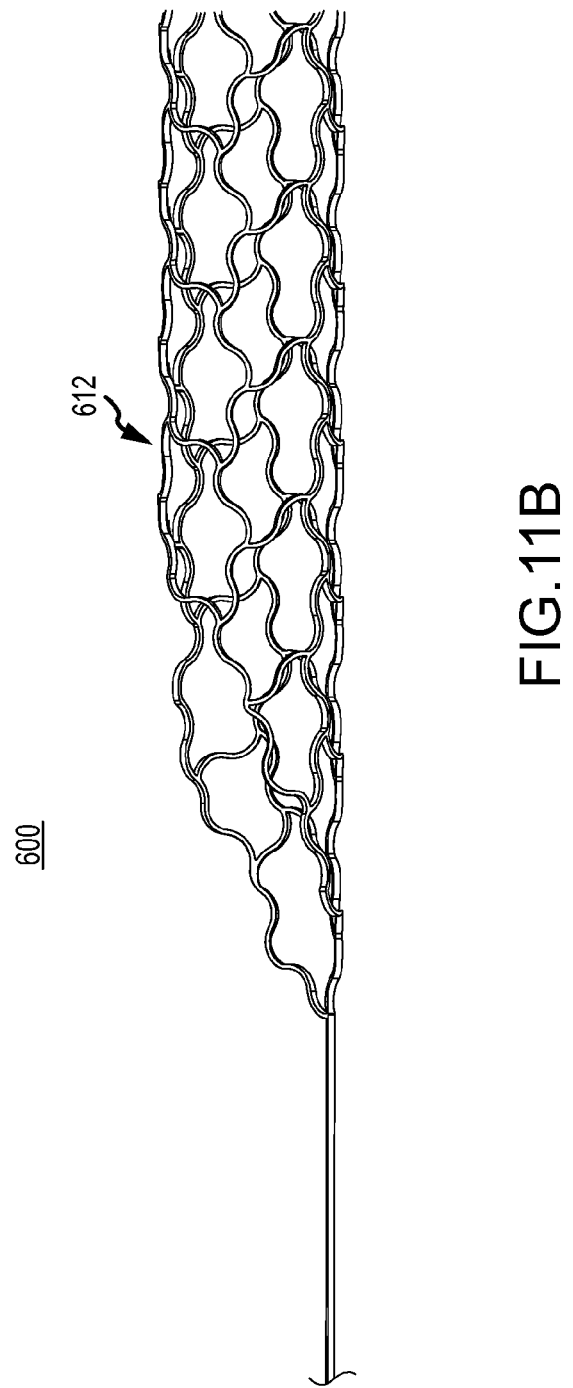

EMBOLIC OBSTRUCTION RETRIEVAL DEVICES AND METHODS

TECHNICAL FIELD

This application relates to devices and methods for the removal of embolic obstructions from the vasculature of a patient.

BACKGROUND

Self-expanding prostheses, such as stents, covered stents, vascular grafts, flow diverters, and the like have been developed to treat ducts within the body. Many of the prostheses have been developed to treat blockages within the vasculature and also aneurysms that occur in the brain. What are needed are devices and methods for removing embolic obstructions, such as, for example, those resulting in ischemic stroke.

SUMMARY OF THE DISCLOSURE

In accordance with one implementation, an embolic obstruction retrieval device is provided having an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of diagonally disposed cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most linear wall segments that, in a two-dimensional view, form first and second substantially linear rail segments that each extend from a position at or near the proximal-most end of the expandable member to a position at or near the cylindrical main body portion. Connected to the proximal-most end of the expandable member is a proximally extending elongate flexible wire having a length and flexibility sufficient for navigating the tortuous vasculature and accessing the embolic obstruction.

In accordance with another implementation, an embolic obstruction retrieval device is provided that includes an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of cell structures that are arranged to induce twisting of the expandable member as the expandable member transitions from the unexpanded position to the expanded position, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most linear wall segments that form first and second substantially linear rail segments that each extend from a position at or near the proximal-most end of the expandable member to a position at or near the cylindrical main body portion. Connected to the proximal-most end of the expandable member is a proximally extending elongate flexible wire having a length and flexibility sufficient for navigating the tortuous vasculature and accessing the embolic obstruction.

In accordance with another implementation, an embolic obstruction retrieval device is provided that includes an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected to form a plurality of diagonally disposed cell structures, the expandable member having a cylindrical portion and a distal end portion, the cell structures in the cylindrical portion extending circumferentially around a longitudinal axis of the expandable member, the cell structures in the distal end portion extending less than circumferentially around the longitudinal axis of the expandable member, the proximal-most cell structures in the main body portion having proximal-most end points. One or more of the proximal-most end points of the expandable member have a proximally extending elongate flexible wire having a length and flexibility sufficient for navigating the tortuous vasculature and accessing the embolic obstruction.

In accordance with another implementation, a kit is provided that includes an elongate flexible wire having a proximal end and a distal end with an elongate self-expandable member attached to the distal end, the self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of diagonally disposed cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most linear wall segments that, in a two-dimensional view, form first and second substantially linear rail segments that each extend from a position at or near the proximal-most end of the expandable member to a position at or near the cylindrical main body portion, the elongate wire and expandable member having a first length, and a delivery catheter having a second length and sufficient flexibility to navigate the tortuous intracranial vasculature of a patient, the delivery catheter having a proximal end, a distal end and an inner diameter, the inner diameter sufficient to receive the expandable member in its unexpanded position and for advancing the unexpanded member from the proximal end to the distal end of the catheter, the second length being less that the first length to allow distal advancement of the expandable member beyond the distal end of the catheter to permit the expandable member to deploy toward its expanded position, the distal end of the catheter and the expandable member configured to permit proximal retraction of the expandable member into the catheter when the expandable member is partially or fully deployed outside the distal end of the catheter.

In accordance with another implementation, a method for removing an embolic obstruction from a vessel of a patient is provided that includes (a) advancing a delivery catheter having an inner lumen with proximal end and a distal end to the site of an embolic obstruction in the intracranial vasculature of a patient so that the distal end of the inner lumen is positioned distal to the embolic obstruction, the inner lumen having a first length, (b) introducing an embolic obstruction retrieval device comprising an elongate flexible wire having a proximal end and a distal end with an elongate self-expandable member attached to the distal end into the proximal end of the inner lumen of the catheter and advancing the self-expandable member to the distal end of the lumen, the self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of diagonally disposed cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the outer cell structures in the proximal end portion having proximal linear wall segments that, in a two-dimensional view, form first and second substantially linear rail segments that each extend from a position at or near the proximal end of the expandable member to a position at or near the cylindrical main body portion, the elongate wire and expandable member in combination having a second length longer than the first length, (c) proximally retracting the delivery catheter sufficient to deploy the self-expandable device so that the one or more of the cell structures entrap at least a portion of the embolic obstruction, and (d) proximally retracting the delivery catheter and self-expandable device to outside the patient. In an alternative implementation, the self-expandable member is partially retracted into the inner lumen of the delivery catheter prior to proximally retracting the delivery catheter and self-expandable device to outside the patient.

BRIEF DESCRIPTION OF THE DRAWINGS

Alternative implementations of the present disclosure are described herein with reference to the drawings wherein:

FIG. 6B is an isometric view of the expandable member illustrated in FIG. 6A.

FIG. 7A illustrates a two-dimensional plane view of an expandable member of an embolic obstruction retrieval device in another embodiment.

FIG. 7B is an isometric view of the expandable member illustrated in FIG. 7A.

FIG. 11B is an isometric view of the expandable member illustrated in FIG. 11A.

DETAILED DESCRIPTION

Figure 1A:
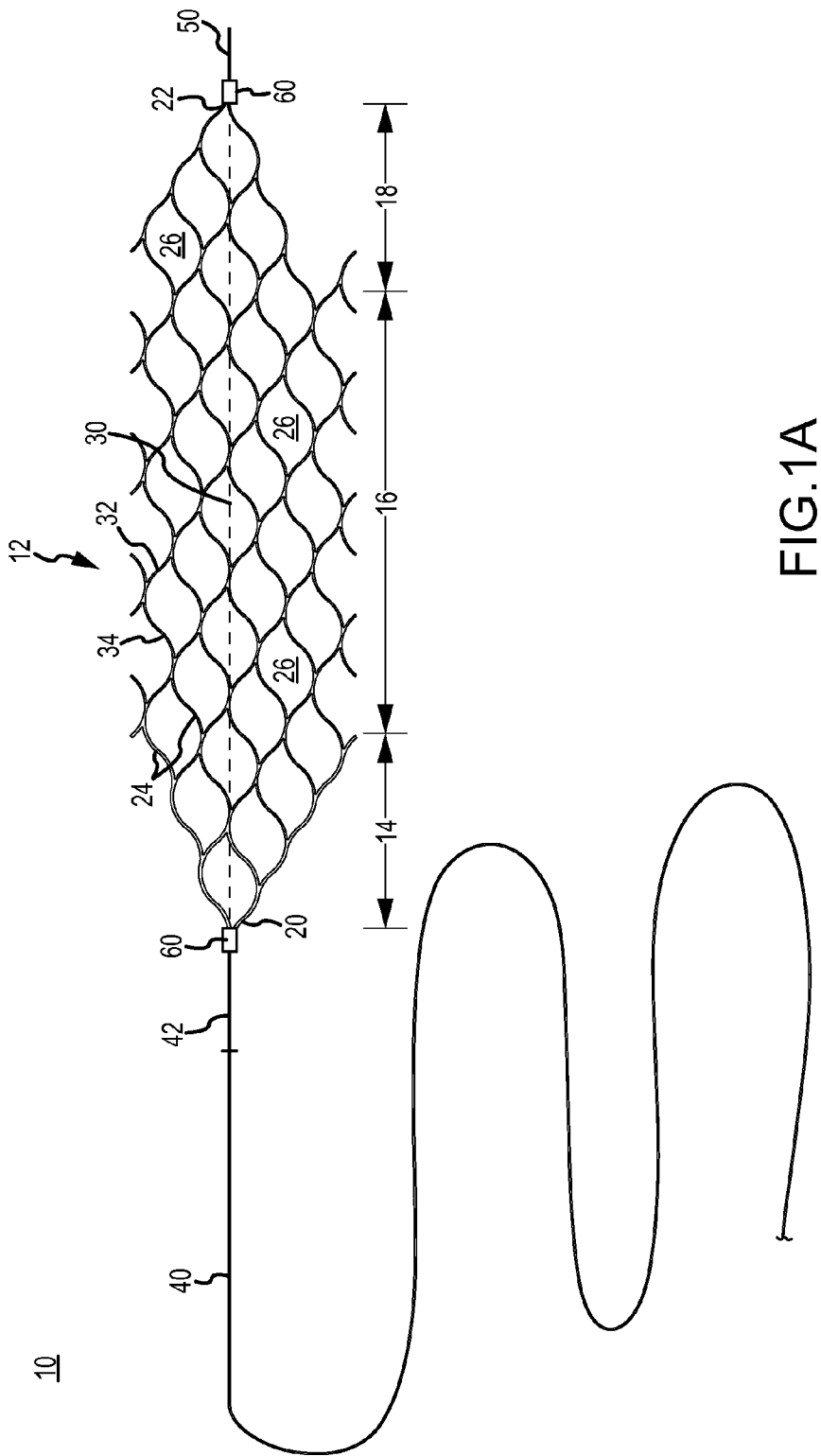
FIG. 1A illustrates a two-dimensional plane view of an expandable member of an embolic obstruction retrieval device in one embodiment.
Figure 1B:
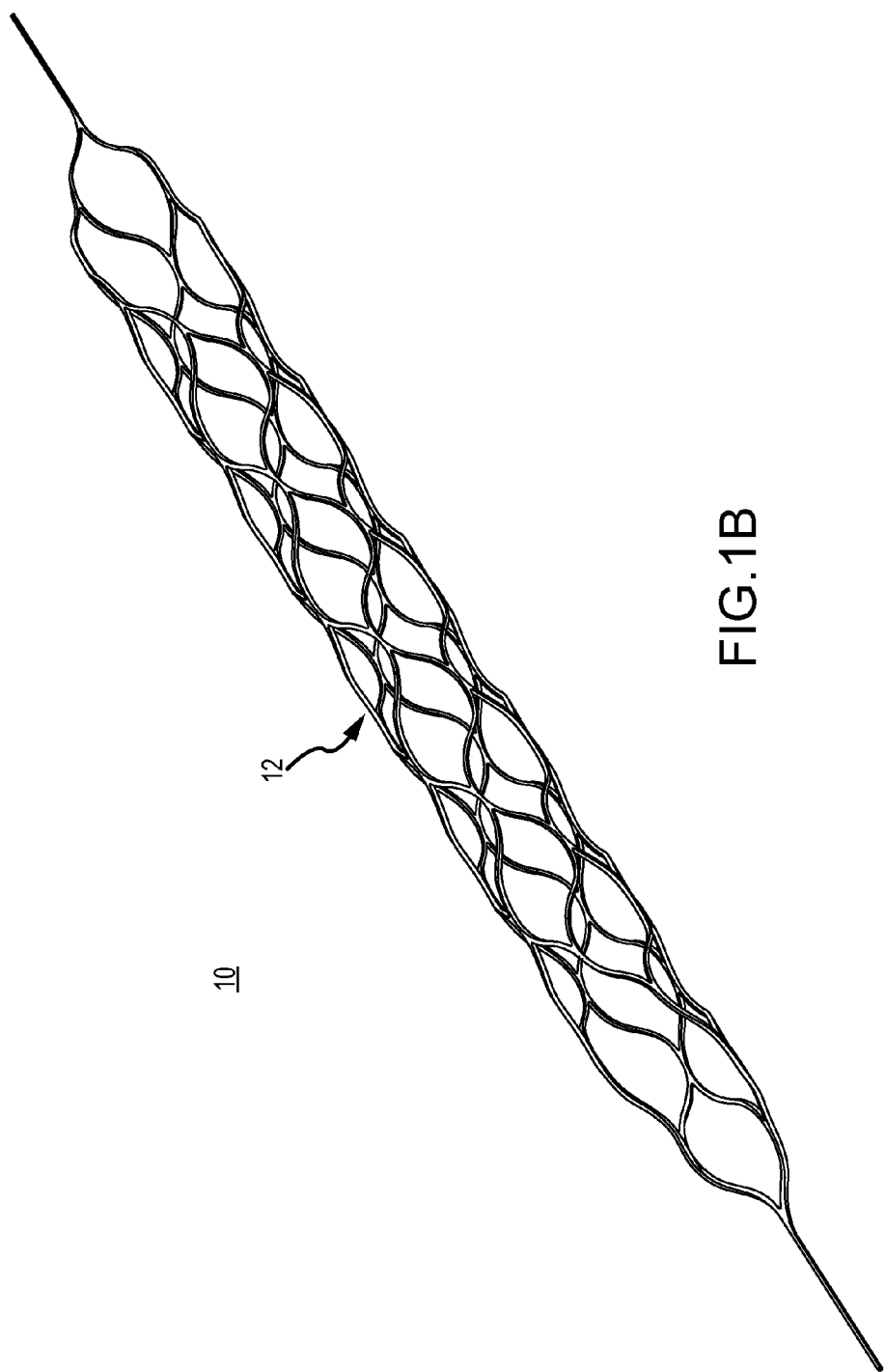
FIG. 1B is an isometric view of the expandable member illustrated in FIG. 1A

FIGS. 1A and 1B illustrate an embolic obstruction retrieval device 10 in accordance with one embodiment of the present invention. FIG. 1A depicts device 10 in a two-dimensional plane view as if the device were cut and laid flat on a surface. FIG. 1B depicts the device in its manufactured and/or expanded tubular configuration. Device 10 includes a self-expandable member 12 that is attached to an elongate flexible wire 40 that extends proximally from the expandable member 12. In one embodiment, the expandable member 12 is made of shape memory material, such as Nitinol, and is preferably laser cut from a tube. In one embodiment, the expandable member 12 has an integrally formed proximally extending wire segment 42 that is used to join the elongate flexible wire 40 to the expandable member 12. In such an embodiment, flexible wire 40 may be joined to wire segment 42 by the use of solder, a weld, an adhesive, or other known attachment method. In an alternative embodiment, the distal end of flexible wire 40 is attached directly to a proximal end 20 of the expandable member 12.

In the embodiment of FIGS. 1A and 1B, expandable member 12 includes a plurality of generally longitudinal undulating elements 24 with adjacent undulating elements being out-of-phase with one another and connected in a manner to form a plurality of diagonally disposed cell structures 26. The expandable member 12 includes a proximal end portion 14, a cylindrical main body portion 16 and a distal end portion 18 with the cell structures 26 in the main body portion 16 extending continuously and circumferentially around a longitudinal axis 30 of the expandable member 12. The cell structures 26 in the proximal end portion 14 and distal end portion 18 extend less than circumferentially around the longitudinal axis 30 of the expandable member 12.

In one embodiment, expandable member 12 has an overall length of about 33.0 millimeters with the main body portion 16 measuring about 16.0 millimeters in length and the proximal and distal end portions 14 and 18 each measuring about 7.0 millimeters in length. In alternative embodiments, the length of the main body portion 16 is generally between about 2.5 to about 3.5 times greater than the length of the proximal and distal end portions 14 and 18.

In use, expandable member 12 is advanced through the tortuous vascular anatomy of a patient to the site of an embolic obstruction in an unexpanded or compressed state (not shown) of a first nominal diameter and is movable from the unexpanded state to a radially expanded state of a second nominal diameter greater than the first nominal diameter for deployment within the embolic obstruction. In alternative exemplary embodiments the first nominal diameter (e.g., average diameter of main body portion 16) ranges between about 0.017 to about 0.030 inches, whereas the second nominal diameter (e.g., average diameter of main body portion 16) is between about 2.5 to about 5.0 millimeters. The dimensional and material characteristics of the cell structures 26 residing in the main body portion 16 of the expandable material 12 are selected to produce sufficient radial force and contact interaction to cause the cell structures 26 to engage with the embolic obstruction in a manner that permits partial or full removal of the embolic obstruction from the patient. In one embodiment the dimensional and material characteristics of the cell structures 26 in the main body portion 16 are selected to produce a radial force per unit length of between about 0.005 N/mm to about 0.020 N/mm.

In the embodiments of FIGS. 1A and 1B, each of the cell structures 26 are shown having the same dimensions with each cell structure including a pair of short struts 32 and a pair of long struts 34. In an exemplary embodiment, struts 32 have a length of between about 0.080 and about 0.100 inches, struts 34 have a length of between about 0.130 and about 0.140 inches, with each of struts 32 and 34 having an as-cut width and thickness of about 0.003 inches and about 0.0045 inches, respectively, and a post-polishing width and thickness of between about 0.0022 inches and about 0.0039 inches, respectively. It is important to note that the present invention is not limited to expandable members 12 having uniform cell structures nor to any particular dimensional characteristics. As an example, in alternative embodiments the cell structures 26 in the proximal and/or distal end portions 14 and 18 are either larger or smaller in size than the cell structures 26 in the main body portion 16. In one embodiment, the cell structures 26 in the proximal and distal end portions 14 and 18 are sized larger than those in the main body portion 16 so that the radial forces exerted in the end portions 14 and 18 are lower than the radial forces exerted in the main body portion 16.

The radial strength along the length of the expandable member 12 may be varied in a variety of ways. One method is to vary the mass (e.g., width and/or thickness) of the struts along the length of the expandable member 12. Another method is to vary the size of the cell structures 26 along the length of the expandable member 12. The use of smaller cell structures will generally provide higher radial forces than those that are larger. Varying the radial force exerted along the length of the expandable member can be particularly advantageous for use in entrapping and retrieving embolic obstructions. For example, in one embodiment the radial force in the distal section of the main body portion 16 of the expandable member 12 in its expanded state is made to be greater than the radial force in the proximal section of the main body portion 16. Such a configuration promotes a larger radial expansion of the distal section of the main body portion 16 into the embolic obstruction as compared to the proximal section. Because the expandable member 12 is pulled proximally during the removal of the embolic obstruction from the patient, the aforementioned configuration will reduce the likelihood of particles dislodging from the embolic obstruction during its removal. In an alternative embodiment the radial force in the proximal section of the main body portion 16 of the expandable member 12 in its expanded state is made to be greater than the radial force in the distal section of the main body portion 16. In yet another embodiment, the main body portion 16 of the expandable member 12 includes a proximal section, a midsection and a distal section with the radial force in the proximal and distal sections being larger than the radial force in the midsection when the expandable member 12 is in an expanded state.

Figure 9:
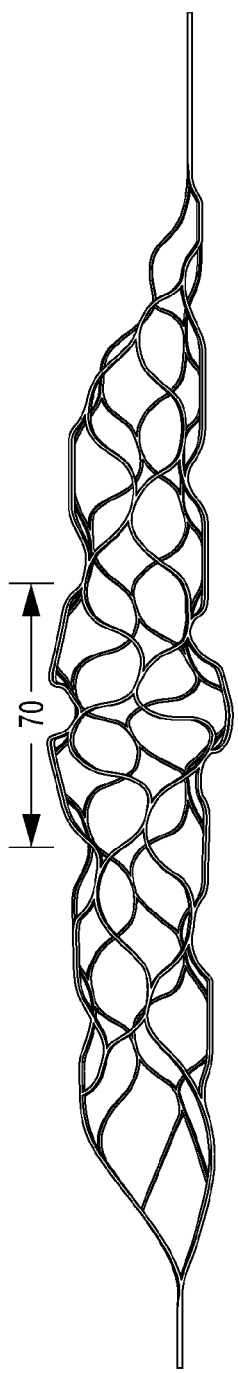
FIG. 9 illustrates an expandable member in an expanded position having a bulge or increased diameter portion.

In alternative embodiments, as exemplified in FIG. 9, the main body portion 16 may include an increased diameter portion or bulge 70 to enhance the expandable member's ability to entrap or otherwise engage with the embolic obstruction. In FIG. 9, a single increased diameter portion 70 is provided within the midsection of main body portion 16. In alternative embodiments, the increased diameter portion 70 may be positioned proximally or distally to the midsection. In yet other embodiments, two or more increased diameter portions 70 may be provided along the length of the main body portion 16. In one implementation, the two or more increased diameter portions 70 have essentially the same manufactured nominal diameter. In another implementation, the distal-most increased diameter portion 70 has a greater manufactured nominal diameter than the proximally disposed increased diameter portions. In alternative exemplary embodiments the nominal diameter of the increased diameter portion 70 is between about 25.0 to about 45.0 percent greater than the nominal diameter of the main body portion 50. For example, in one embodiment, the nominal expanded diameter of main body portion 16 is about 3.0 millimeters and the nominal diameter of the increased diameter portion 70 is about 4.0 millimeters. In another embodiment the nominal expanded diameter of main body portion 16 is about 3.50 millimeters and the nominal diameter of the increased diameter portion 70 is about 5.00 millimeters. In one embodiment, the one or more increased diameter portions 70 are formed by placing an expandable mandrel into the internal lumen of the main body portion 16 and expanding the mandrel to create the an increased diameter portion 70 of a desired diameter. In another embodiment, one or more of the increased diameter portions 70 are formed by placing a mandrel of a given width and diameter into the main body portion 16 and then crimping the expandable member 12 in a manner to cause at least a portion of the main body portion 16 to be urged against the mandrel.

Figure 2:
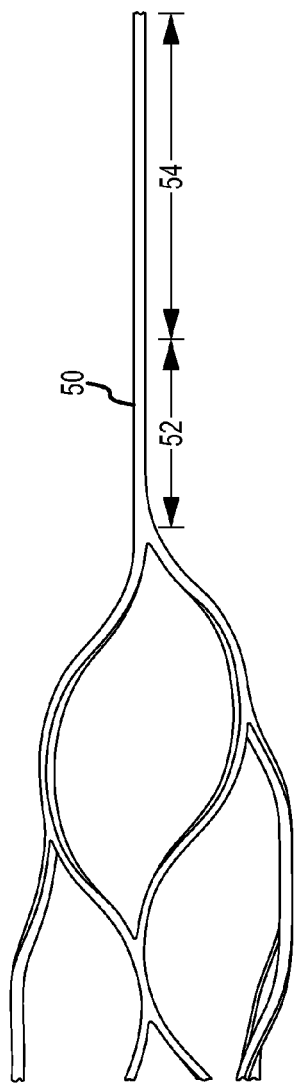
FIG. 2 illustrates a distal wire segment that extends distally from an expandable member in one embodiment.
Figure 3:
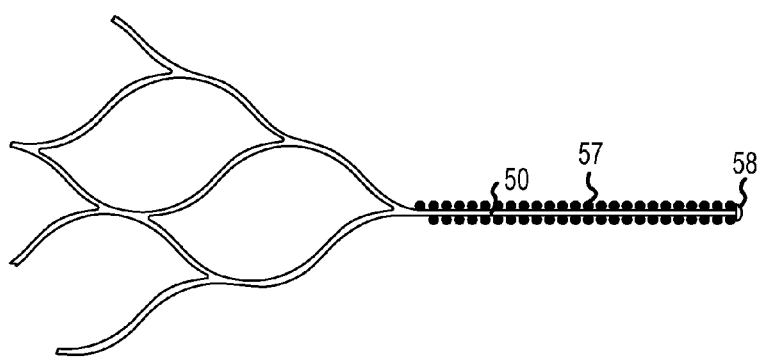
FIG. 3 illustrates the distal end of an expandable member having an atraumatic tip.

In one implementation, a distal wire segment 50, that is attached to or integrally formed with expandable member 12, extends distally from the distal end 22 of the expandable member 12 and is configured to assist in guiding the delivery of the expandable member to the treatment site of a patient. FIG. 2 shows a distal wire segment 50 in one embodiment having a first section 52 of a uniform cross-section and a second section 54 having a distally tapering cross-section. In an exemplary embodiment, the first section 52 has a length of about 3.0 millimeters and an as-cut cross-sectional dimension of about 0.0045 inches by about 0.003 inches, and whereas the second section 54 has a length of about 4.0 millimeters and tapers to a distal-most, as-cut, cross-sectional dimension of about 0.002.inches by about 0.003 inches. Post-polishing of the device generally involves an etching process that typically results in a 40% to 50% reduction in the as-cut cross-sectional dimensions. In another embodiment, as depicted in FIG. 3, the distal wire segment 50 is bound by a spring member 57 of a uniform diameter and is equipped with an atraumatic distal tip 58. In alternative embodiments, the spring element 57 and/or the atraumatic tip 58 are made or coated with of a radiopaque material, such as, for example, platinum.

In one embodiment, as will be described in more detail below, the expandable member 12 is delivered to the treatment site of a patient through the lumen of a delivery catheter that has been previously placed at the treatment site. In an alternative embodiment, the embolic obstruction retrieval device 10 includes a sheath that restrains the expandable member 12 in a compressed state during delivery to the treatment site and which is proximally retractable to cause the expandable member 12 to assume an expanded state. In either case, the expandable member 12 in the expanded state engages the embolic obstruction, for example by embedding itself into the obstruction, and is removable from the patient by pulling on a portion of the elongate flexible wire 40 residing outside the patient until the expandable member 12 and at least a portion of the embolic obstruction are removed from the patient.

The use of interconnected and out-of-phase undulating elements 24 to create at least some of the cell structures 26 provides several advantages. First, the curvilinear nature of the cell structures 26 enhances the flexibility of the expandable member 12 during its delivery through the tortuous anatomy of the patient to the treatment site. In addition, the out-of-phase relationship between the undulating elements facilitates a more compact nesting of the expandable member elements permitting the expandable member 12 to achieve a very small compressed diameter. A particular advantage of the expandable member strut pattern shown in FIG. 1A, and the various other embodiments described herein, is that they enable sequential nesting of the expandable member elements which permit the expandable members to be partially or fully deployed and subsequently withdrawn into the lumen of a delivery catheter. The out-of-phase relationship also results in a diagonal orientation of the cell structures 26 which may induce a twisting action as the expandable member 12 transitions from a compressed state to an expanded state that helps the expandable member to better engage with the embolic obstruction. In alternative embodiments, the cell structures 26 of the expandable member 12 are specifically arranged to produce a desired twisting action during expansion of the expandable member 12. In this manner, different expandable members each having different degrees of twisting action may be made available to treat different types of embolic obstructions.

To enhance visibility of the device under fluoroscopy, the expandable member may be fully or partially coated with a radiopaque material, such as tungsten, platinum, platinum/iridium, tantalum and gold. Alternatively, or in conjunction with the use of a radiopaque coating, radiopaque markers 60 may be positioned at or near the proximal and distal ends 20 and 22 of the expandable device and/or along the proximal and distal wire segments 42 and 50 and/or on selected expandable member strut segments. In one embodiment, the radiopaque markers 60 are radiopaque coils, such as platinum coils.

Figure 4A:
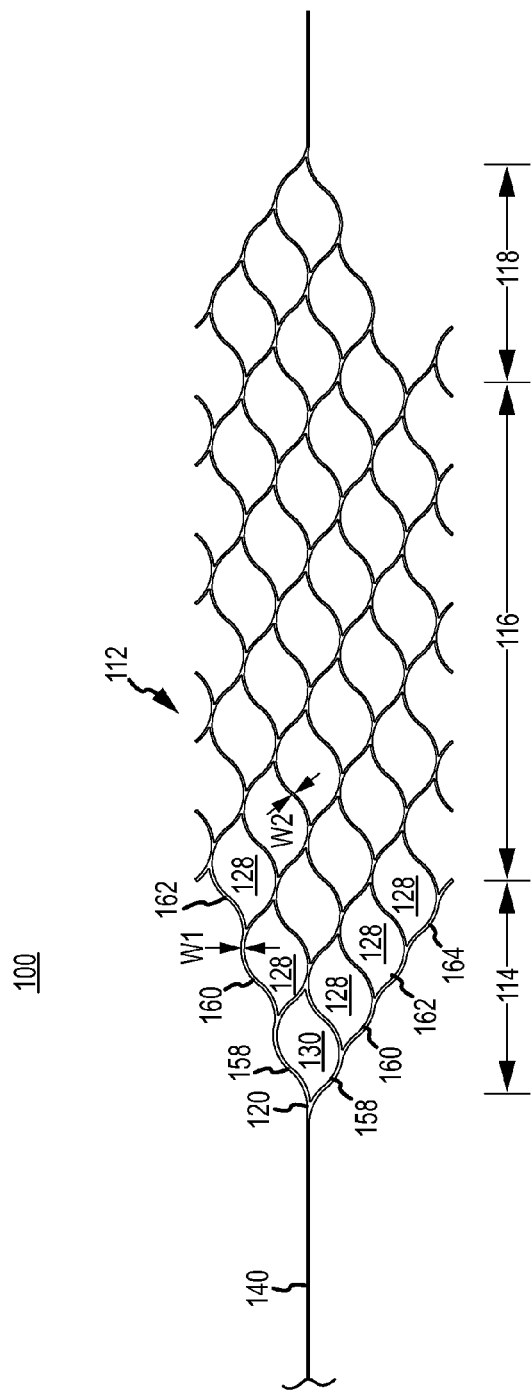
FIG. 4A illustrates a two-dimensional plane view of an expandable member of an embolic obstruction retrieval device in another embodiment.
Figure 4B:
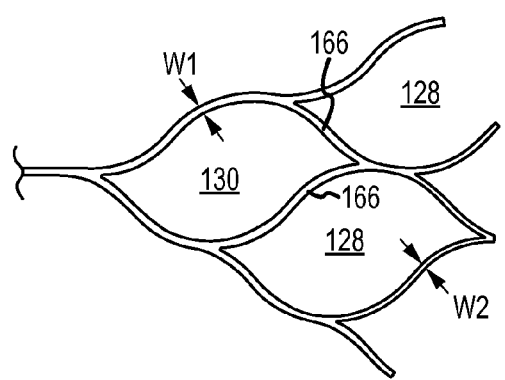
FIG. 4B is an enlarged view of the proximal-most segment of the expandable member illustrated in FIG. 4A.

FIG. 4A depicts an embolic obstruction retrieval device 100 in a two-dimensional plane view in another embodiment of the present invention. In its manufactured and/or expanded tubular configuration, device 100 has a similar construction as device 10 shown in FIG. 1B. Like device 10 described above in conjunction with FIGS. 1A and 1B, device 100 includes a self-expandable member 112 that is coupled to an elongate flexible wire 140. The expandable member 112 includes a proximal end portion 114, a cylindrical main body portion 116 and a distal end portion 118. As mentioned above, delivery of the expandable member 112 in its unexpanded state to the treatment site of a patient is accomplished in one manner by placing the expandable member 112 into the proximal end of a delivery catheter and pushing the expandable member 112 through the lumen of the delivery catheter until it reaches a distal end of the catheter that has been previously placed at or across the treatment site. The proximally extending elongate flexible wire 140 which is attached to or coupled to the proximal end 120 of the expandable member 112 is designed to transmit a pushing force applied to it to its connection point with the elongate flexible member 112. As shown in FIG. 4A, and in more detail in FIG. 4B, device 100 is distinguishable from the various embodiments of device 10 described above in that the proximal-most cell structures 128 and 130 in the proximal end portion 114 include strut elements having a width dimension W1 larger than the width dimension W2 of the other strut elements within the expandable member 112. As shown, the proximal-most wall sections 160, 162 and 164 of cell structures 128 are made of struts having width W1. Moreover, all the struts of the proximal-most cell structure 130 have an enhanced width W1. The inclusion and placement of the struts with width W1 provides several advantages. One advantage is that they permit the push force applied by the distal end of the elongate wire 140 to the proximal end 120 of elongate member 112 to be more evenly distributed about the circumference of the expandable member 112 as it is being advanced through the tortuous anatomy of a patient. The more evenly distributed push force minimizes the formation of localized high force components that would otherwise act on individual or multiple strut elements within the expandable member 112 to cause them to buckle. Also, by including the struts of width W1 in the peripheral regions of proximal end portion 114, they greatly inhibit the tendency of the proximal end portion 114 to buckle under the push force applied to it by elongate wire 140. In one exemplary embodiment the as-cut width dimension W1 is about 0.0045 inches and the as-cut width dimension W2 is about 0.003 inches. As discussed above, post-polishing of the device generally involves an etching process that typically results in a 40% to 50% reduction in the as-cut cross-sectional dimensions.

It is important to note that although the width dimension W1 is shown as being the same among all struts having an enhanced width, this is not required. For example, in one embodiment wall segments 158 may have an enhanced width dimension greater than the enhanced width dimension of wall segments 160, and wall segments 160 may have an enhanced width dimension greater than the enhanced width dimension of wall segments 162, and so on. Moreover, the inner strut elements 166 of the proximal-most cell structure 130 may have an enhanced width dimension less than the enhanced width dimensions of struts 158. Also, in alternative embodiments, the radial thickness dimension of struts 158, 160, 162, 164, etc. may be enhanced in lieu of the width dimension or in combination thereof.

Figure 5:
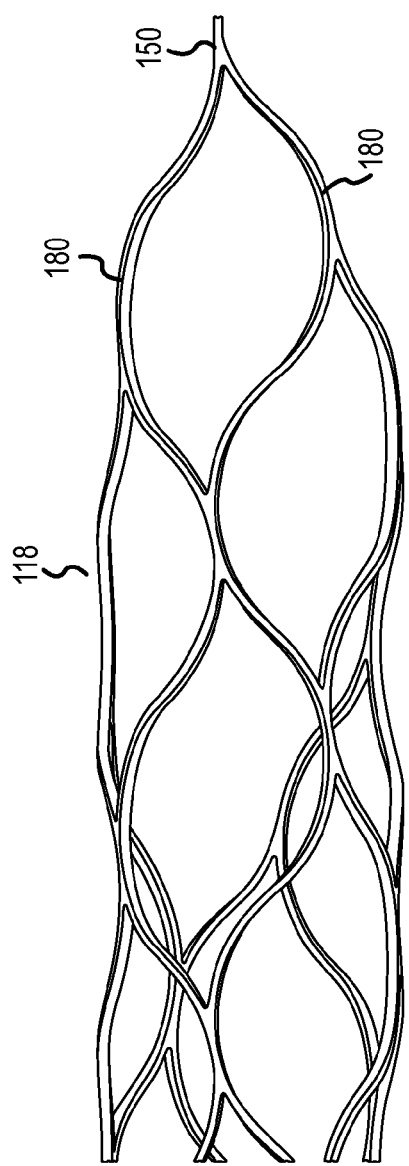
FIG. 5 illustrates a distal end of an expandable member in one embodiment.

In yet another embodiment, as shown in FIG. 5, some of the strut elements 180 in the distal end portion 118 of the expandable member 112 have a mass greater than that of the other struts to resist buckling and possible breaking of the struts as device 100 is advanced to a treatment site of a patient. In the embodiment shown, struts 180 are dimensioned to have the same width as distal wire segment 150. In alternative embodiments, the thickness dimension of struts 182 may be enhanced in lieu of the width dimension or in combination thereof.

Figure 6A:
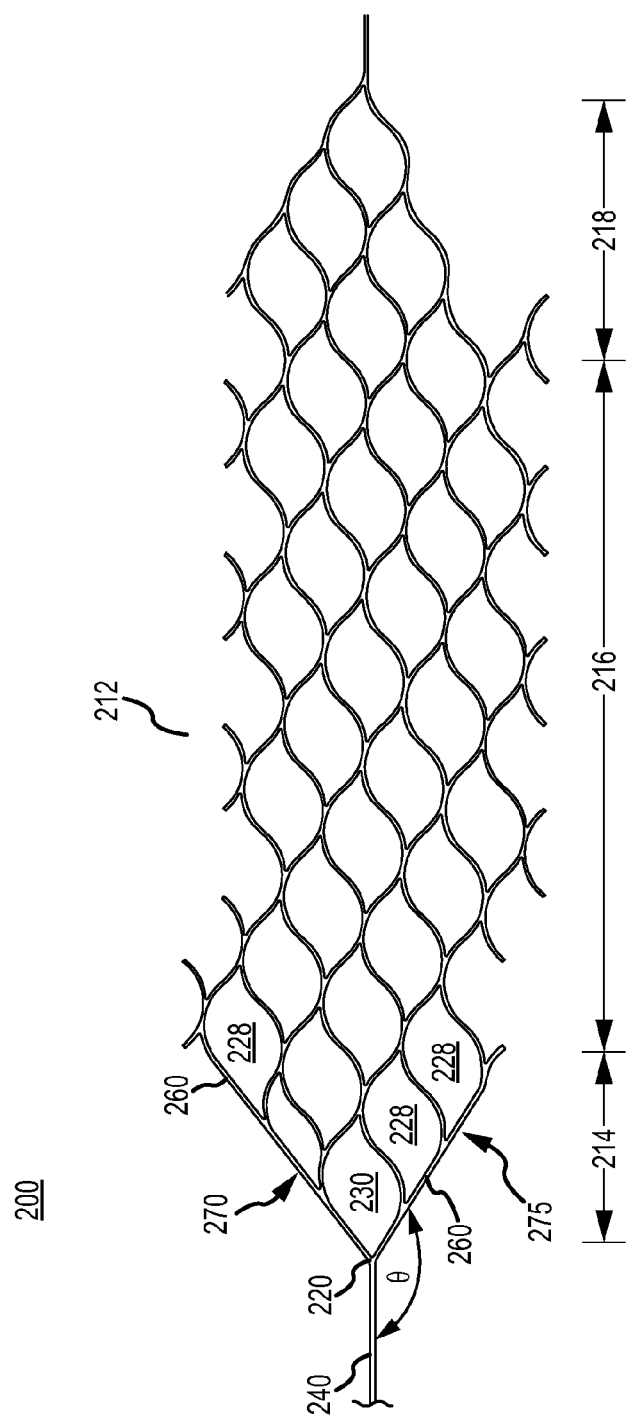
FIG. 6A illustrates a two-dimensional plane view of an expandable member of an embolic obstruction retrieval device in another embodiment.

FIGS. 6A and 6B illustrate an embolic obstruction retrieval device 200 in accordance with another embodiment of the present invention. FIG. 6A depicts device 200 in a two-dimensional plane view as if the device were cut and laid flat on a surface. FIG. 6B depicts the device in its manufactured and/or expanded tubular configuration. Device 200 includes an expandable member 212 having a proximal end portion 214, a cylindrical main body portion 216 and a distal end portion 218 with an elongate flexible wire 240 attached to or otherwise coupled to the proximal end 220 of the expandable member. The construction of device 200 is similar to device 100 described above in conjunction with FIG. 4A except that the proximal wall segments 260 of cell structures 228 and 230 comprise linear strut elements of an enhanced width dimension W1 as viewed in the two dimension plane view of FIG. 6A. In a one embodiment, the linear strut elements 260 are aligned to form continuous and substantially linear rail segments 270 that extend from the proximal end 220 of proximal end portion 114 to a proximal-most end of main body portion 216 (again, as viewed in the two dimension plane view of FIG. 6A) and preferably are of the same length. When the pattern of FIG. 6A is applied to laser cutting a tubular structure, the resulting expandable member configuration is that as shown in FIG. 6B. As shown in FIG. 6B, rail segments 270 are not in fact linear but are of a curved and non-undulating shape. This configuration advantageously provides rail segments 270 devoid of undulations thereby enhancing the rail segments' ability to distribute forces and resist buckling when a push force is applied to them. In alternative preferred embodiments, the angle θ between the wire segment 240 and rail segments 270 ranges between about 140 degrees to about 150 degrees.

FIGS. 7A and 7B illustrate an embolic obstruction retrieval device 300 in accordance with another embodiment of the present invention. FIG. 7A depicts device 300 in a two-dimensional plane view as if the device were cut and laid flat on a surface. FIG. 7B depicts the device in its manufactured and/or expanded tubular configuration. Device 300 includes an expandable member 312 having a proximal end portion 314, a cylindrical main body portion 316 and a distal end portion 318 with an elongate flexible wire 340 attached to or otherwise coupled to the proximal end 320 of the expandable member. The construction of device 300 is similar to device 200 described above in conjunction with FIGS. 6A and 6B except that the proximal-most cell structure 330 comprises a substantially diamond shape as viewed in the two-dimensional plane of FIG. 7A. The substantially diamond-shaped cell structure includes a pair of outer strut elements 358 and a pair of inner strut elements 360, each having an enhanced width W1 and/or enhanced thickness dimension as previously discussed in conjunction with the embodiments of FIGS. 4 and 6. In alternative preferred embodiments, the inner strut elements 360 intersect the outer strut elements 358 at an angle β between about 25.0 degrees to about 45.0 degrees as viewed in the two-dimensional plane view of FIG. 7A. Maintaining the angular orientation between the inner and outer struts within in this range enhances the pushabilty of the expandable member 312 without the occurrence of buckling and without substantially affecting the expandable member's ability to assume a very small compressed diameter during delivery.

Figure 7C:
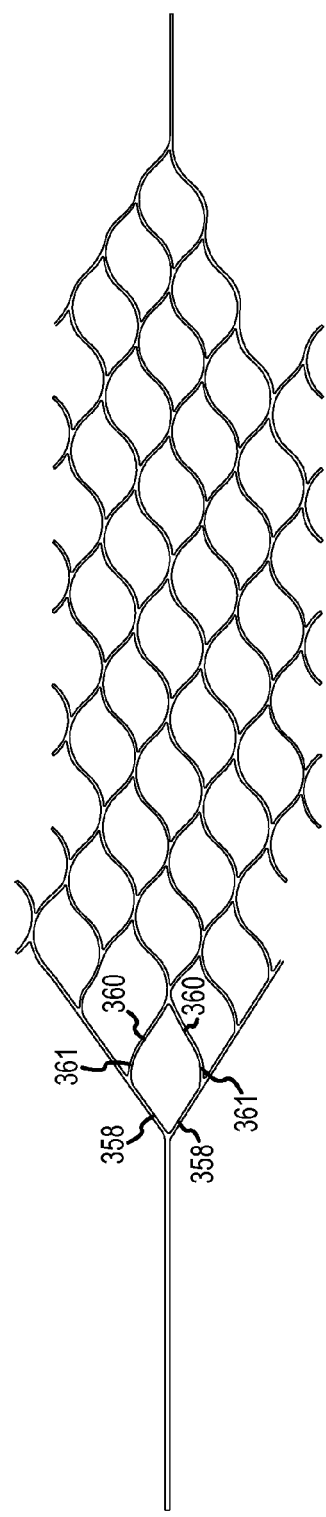
FIG. 7C illustrates a two-dimensional plane view of an expandable member of an embolic obstruction retrieval device in another embodiment.

In one embodiment, the inner strut elements 360 have a mass less than that of the outer strut elements 358 that enables them to more easily bend as the expandable member 312 transitions from an expanded state to a compressed state. This assists in achieving a very small compressed diameter. In another embodiment, as shown in FIG. 7C, the inner strut elements 360 are coupled to the outer strut elements 358 by curved elements 361 that enable the inner strut elements 360 to more easily flex when the expandable member 312 is compressed to its delivery position.

Figure 8:
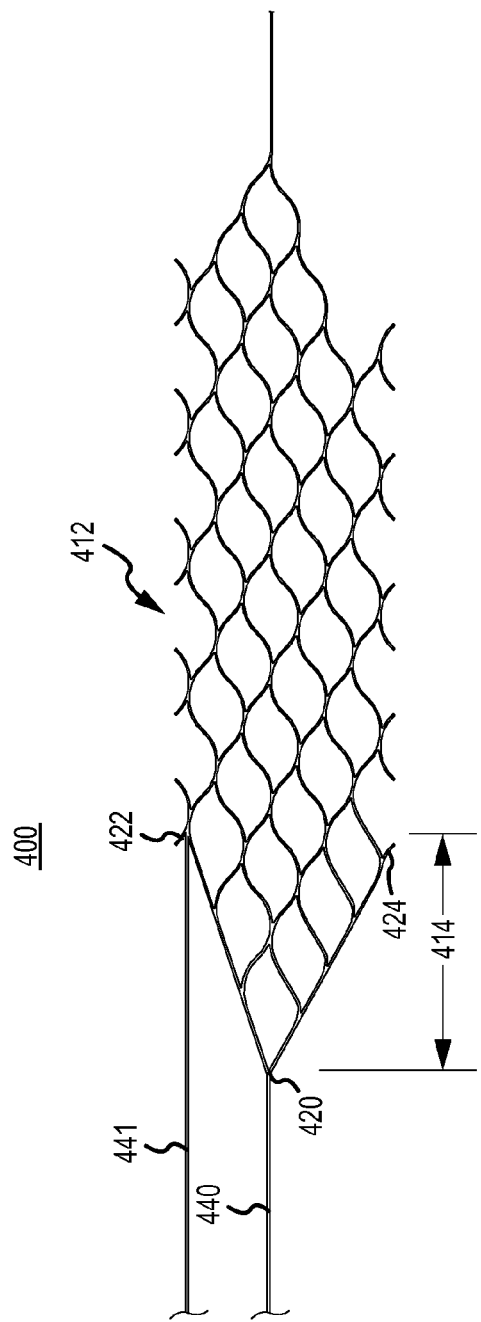
FIG. 8 illustrates a two-dimensional plane view of an expandable member of an embolic obstruction retrieval device in another embodiment.

FIG. 8 illustrates an alternative embodiment of an embolic obstruction retrieval device 400. Device 400 has a similar construction to that of device 200 depicted in FIGS. 6A and 6B with the exception that the expandable member 412 of device 400 is connected at its proximal end portion 414 with two distally extending elongate flexible wires 440 and 441. As illustrated, wire 440 is attached to or otherwise coupled to the proximal-most end 420 of proximal end portion 414, while wire 441 is attached to or otherwise coupled to the distal-most end 422 of the proximal end portion 414 at the junction with rail segment 470. In yet another embodiment, an additional elongate flexible wire (not shown) may be attached to the distal-most end 424. The use of two or more elongate flexible wires 440 and 441 to provide pushing forces to the proximal end portion 414 of elongate member 412 advantageously distributes the pushing force applied to the proximal end portion 414 to more than one attachment point.

Figure 10:
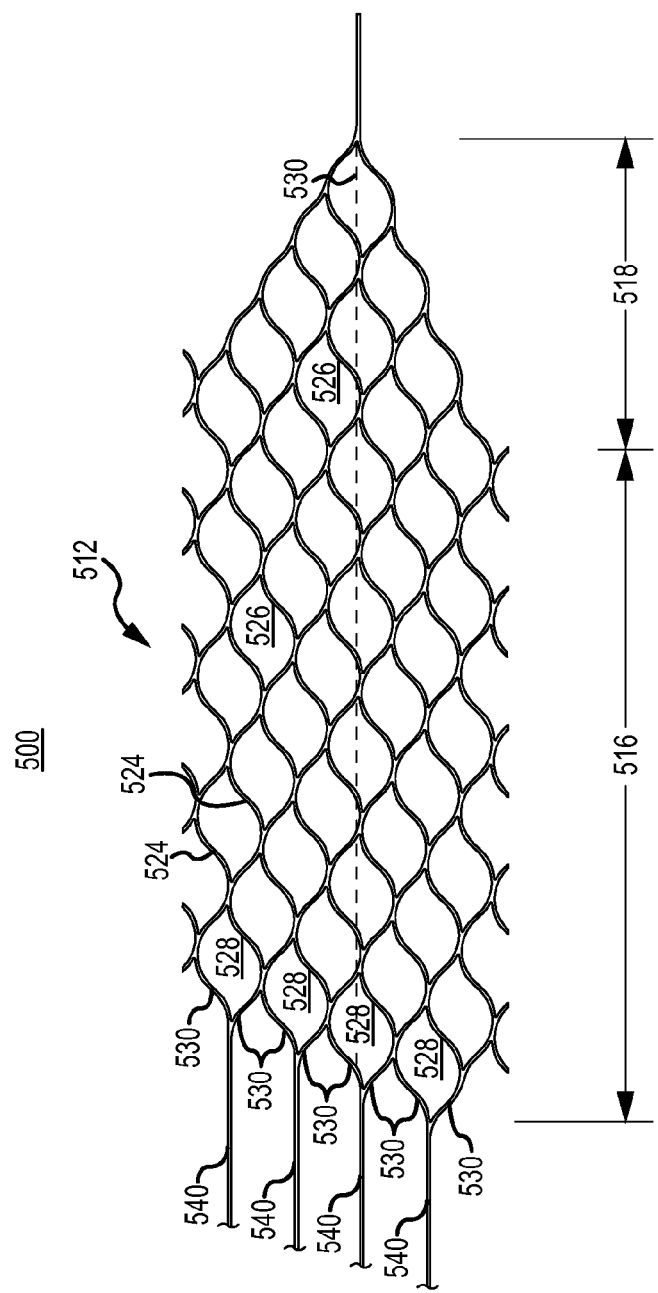
FIG. 10 illustrates a two-dimensional plane view of an expandable member of an embolic obstruction retrieval device in another embodiment.

FIG. 10 illustrates a two-dimensional plane view of an embolic obstruction retrieval device 500 in another embodiment of the present invention. In the embodiment of FIG. 10, expandable member 512 includes a plurality of generally longitudinal undulating elements 524 with adjacent undulating elements being out-of-phase with one another and connected in a manner to form a plurality of diagonally disposed cell structures 526. The expandable member 512 includes a cylindrical portion 516 and a distal end portion 518 with the cell structures 526 in the main body portion 516 extending continuously and circumferentially around a longitudinal axis 530 of the expandable member 512. The cell structures 526 in the distal end portion 518 extend less than circumferentially around the longitudinal axis 530 of the expandable member 512. Attached to or otherwise coupled to each of the proximal-most cell structures 528 are proximally extending elongate flexible wires 540. The use of multiple elongate flexible wires 540 enables the pushing force applied to the proximal end of the expandable member 512 to be more evenly distributed about its proximal circumference. In another embodiment, although not shown in FIG. 10, the proximal-most strut elements 528 have a width and/or thickness greater than the struts in the other portions of the expandable member 512. Such a feature further contributes to the push force being evenly distributed about the circumference of the expandable member 512 and also inhibits the strut elements directly receiving the push force from buckling.

Figure 11A:
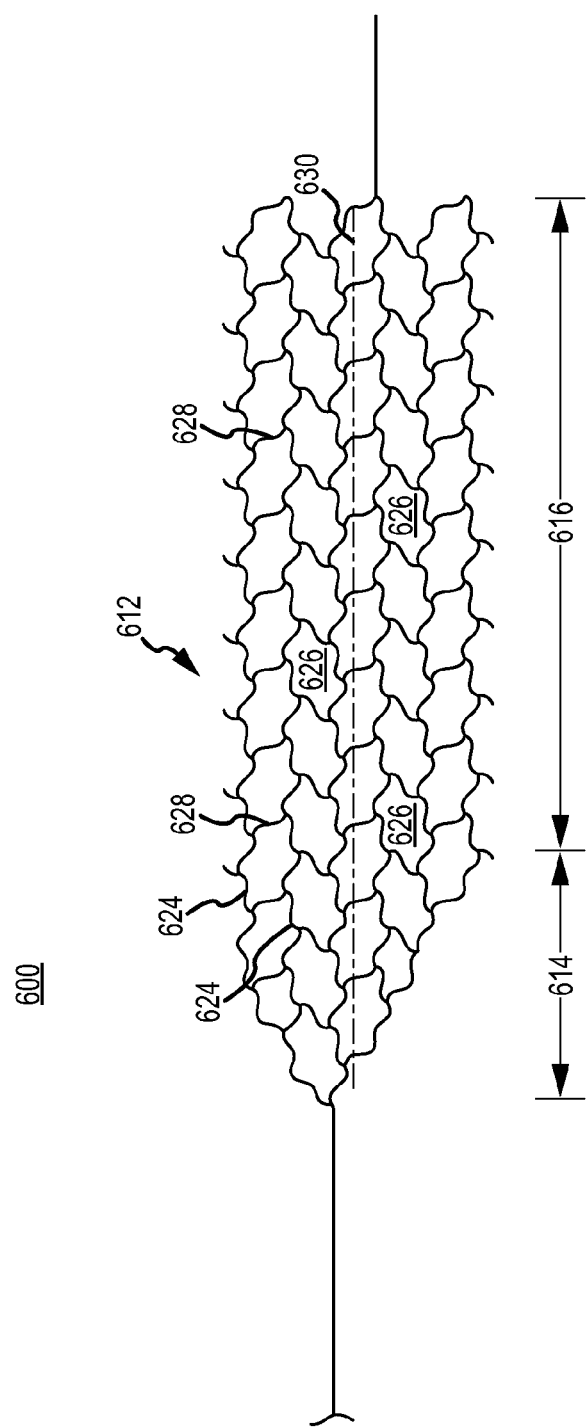
FIG. 11A illustrates a two-dimensional plane view of an expandable member of an embolic obstruction retrieval device in one implementation.

FIGS. 11A and 11B illustrate an embolic obstruction retrieval device 600 in accordance with another embodiment of the present invention. FIG. 11A depicts device 600 in a two-dimensional plane view as if the device were cut and laid flat on a surface. FIG. 11B depicts the device in its manufactured and/or expanded tubular configuration. In the embodiment of FIGS. 11A and 11B, expandable member 612 includes a plurality of generally longitudinal undulating elements 624 with adjacent undulating elements being interconnected by a plurality of curved connectors 628 to form a plurality of closed-cell structures 626 disposed about the length of the expandable member 612. In the embodiment shown, the expandable member 612 includes a proximal end portion 614 and a cylindrical portion 616 with the cell structures 626 in the cylindrical portion 616 extending continuously and circumferentially around a longitudinal axis 630 of the expandable member 612. The cell structures 626 in the proximal end portion 614 extend less than circumferentially around the longitudinal axis 630 of the expandable member 612. In an alternative embodiment, the expandable member 612 includes a proximal end portion, a cylindrical main body portion and a distal end portion, much like the expandable member 12 depicted in FIGS. 1A and 1B. In such an embodiment, the cell structures 626 in the distal end portion of the expandable member would extend less than circumferentially around the longitudinal axis 630 of the expandable member 612 in a manner similar to the proximal end portion 614 shown in FIG. 11A.

Figure 12:
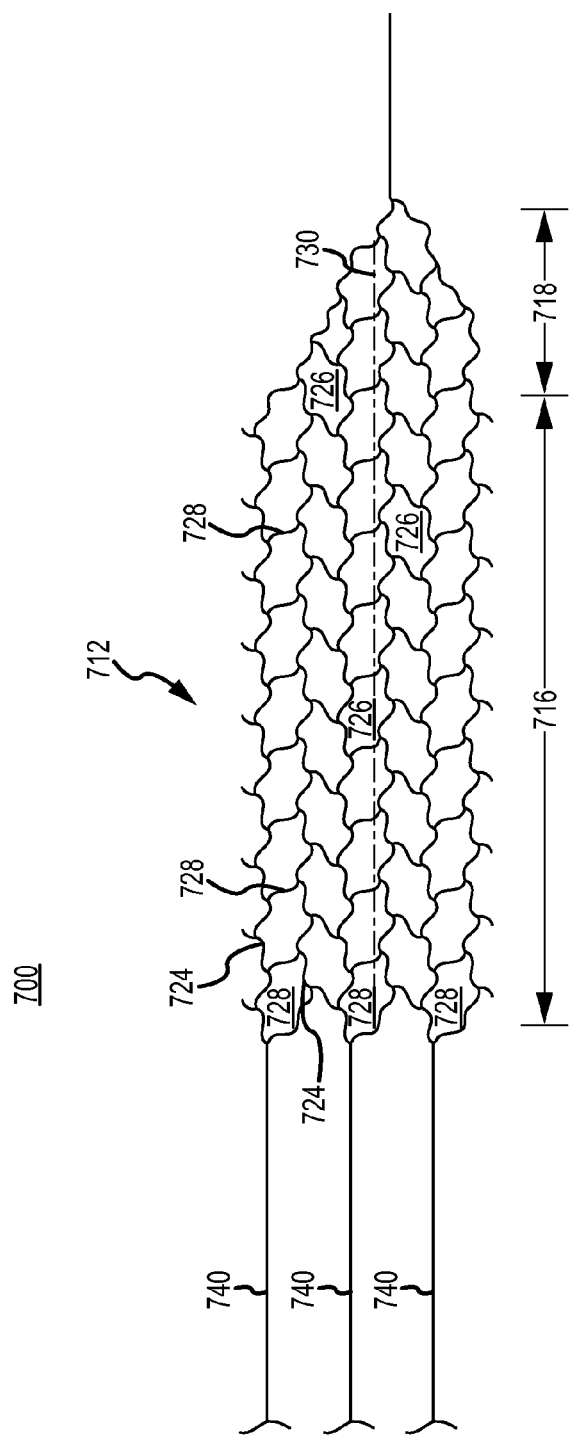
FIG. 12 illustrates a two-dimensional plane view of an expandable member of an embolic obstruction retrieval device in another implementation.

FIG. 12 illustrates an embolic obstruction retrieval device 700 in accordance with another embodiment of the present invention. FIG. 12 depicts device 700 in a two-dimensional plane view as if the device were cut and laid flat on a surface. In the embodiment of FIG. 12, expandable member 712 includes a plurality of generally longitudinal undulating elements 724 with adjacent undulating elements being interconnected by a plurality of curved connectors 728 to form a plurality of closed-cell structures 726 disposed about the length of the expandable member 712. In the embodiment shown, the expandable member 712 includes a cylindrical portion 716 and a distal end portion 718 with the cell structures 726 in the cylindrical portion 716 extending continuously and circumferentially around a longitudinal axis 730 of the expandable member 712. The cell structures 726 in the distal end portion 718 extend less than circumferentially around the longitudinal axis 730 of the expandable member 712. In a manner similar to that described in conjunction with the embodiment of FIG. 10, attached to or otherwise coupled to each of the proximal-most cell structures 728 are proximally extending elongate flexible wires 740. This arrangement enables the pushing force applied to the proximal end of the expandable member 712 to be more evenly distributed about its proximal circumference. In another embodiment, although not shown in FIG. 12, the proximal-most strut elements 730 have a width and/or thickness greater than the struts in the other portions of the expandable member 712. Such a feature further contributes to the push force being evenly distributed about the circumference of the expandable member 712 and also inhibits the strut elements directly receiving the push force from buckling.

Figure 13A:
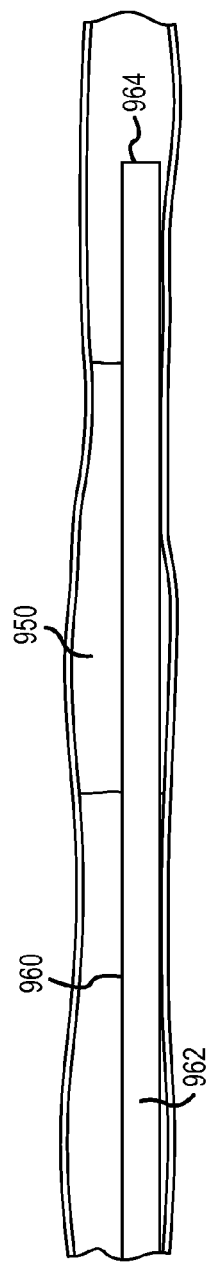
FIGS. 13A through 13C illustrate a method for retrieving an embolic obstruction in accordance with one implementation.
Figure 13B:
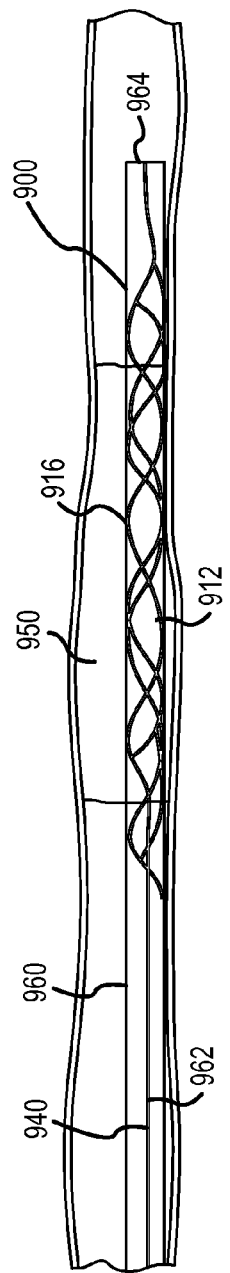
Figure 13C:
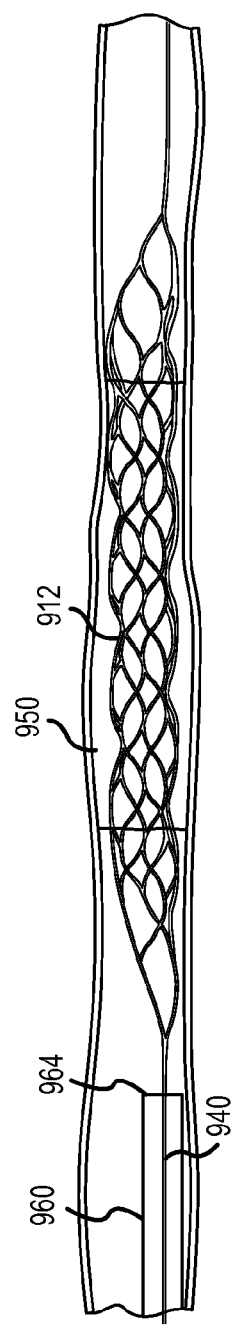

As previously discussed, in use, the expandable members of the present invention are advanced through the tortuous vascular anatomy of a patient to the site of an embolic obstruction in an unexpanded or compressed state of a first nominal diameter and are movable from the unexpanded state to a radially expanded state of a second nominal diameter greater than the first nominal diameter for deployment within the embolic obstruction. One manner of delivering and deploying expandable member 912 at the site of an embolic obstruction 950 is shown in FIGS. 13A through 13C. As shown in FIG. 13A, a delivery catheter 960 having an inner lumen 962 is advanced to the site of the embolic obstruction 950 so that its distal end 964 is positioned distal to the obstruction. After the delivery catheter 960 is in position at the embolic obstruction 950, the retrieval device 900 is placed into the delivery catheter by introducing the expandable member 912 into a proximal end of the delivery catheter (not shown) and then advancing the expandable member 912 through the lumen 962 of the delivery catheter by applying a pushing force to elongate flexible wire 940. By the use of radiopaque markings and/or coatings positioned on the delivery catheter 960 and device 900, the expandable member 912 is positioned at the distal end of the delivery catheter 960 as shown in FIG. 13B so that the main body portion 916 is longitudinally aligned with the obstruction 950. Deployment of the expandable member 912 is achieved by proximally withdrawing the delivery catheter 960 while holding the expandable member 912 in a fixed position as shown in FIG. 13C. Once the expandable member 912 has been deployed to an expanded position within the obstruction 950, the expandable member 912 is retracted, along with the delivery catheter 960, to a position outside the patient. In one embodiment, the expandable member 912 is first partially retracted to engage with the distal end 964 of the delivery catheter 960 prior to fully retracting the devices from the patient.

In one embodiment, once the expandable member 912 is expanded at the obstruction 950, it is left to dwell there for a period of time in order to create a perfusion channel through the obstruction that causes the obstruction to be lysed by the resultant blood flow passing through the obstruction. In such an embodiment, it is not necessary that the expandable member 912 capture a portion of the obstruction 950 for retrieval outside the patient. When a sufficient portion of the obstruction 950 has been lysed to create a desired flow channel through the obstruction, or outright removal of the obstruction is achieved by the resultant blood flow, the expandable member 912 may be withdrawn into the delivery catheter 960 and subsequently removed from the patient.

In another embodiment, the expandable member 912 is expanded at the obstruction 950 and left to dwell there for a period of time in order to create a perfusion channel through the obstruction that causes the obstruction to be acted on by the resultant flow in a manner that makes the embolic obstruction more easily capturable by the expandable member and/or to make it more easily removable from the vessel wall of the patient. For example, the blood flow created through the embolic obstruction may be made to flow through the obstruction for a period of time sufficient to change the morphology of the obstruction that makes it more easily captured by the expandable member and/or makes it more easily detachable from the vessel wall. As in the preceding method, the creation of blood flow across the obstruction 950 also acts to preserve tissue. In one embodiment, the blood flow through the obstruction may be used to lyse the obstruction. However, in this modified method, lysing of the obstruction is performed for the purpose of preparing the obstruction to be more easily captured by the expandable member 912. When the obstruction 950 has been properly prepared, for example by creating an obstruction 950 of a desired nominal inner diameter, the expandable member 912 is deployed from the distal end 964 of the delivery catheter 940 to cause it to engage with the obstruction. Removal of all, or a portion, of the obstruction 950 from the patient is then carried out in a manner similar to that described above.

In yet another embodiment, once the expandable member 912 has been delivered and expanded inside the obstruction 950, it may be detached from the elongate wire 940 for permanent placement within the patient. In such an embodiment, the manner in which the elongate wire 940 is attached to the expandable member 912 allows the two components to be detached from one another. This may be achieved, for example, by the use of a mechanical interlock or an erodable electrolytic junction between the expandable member 912 and the elongate wire 940.

As described herein, the expandable members of the various embodiments may or may not include distal wire segments that are attached to their distal ends. In alternative preferred embodiments, embolic retrieval devices that are configured to permanently place an expandable member at the site of an embolic obstruction do not include distal wire segments attached to the distal ends of the expandable members.

One advantage associated with the expandable member cell patterns of the present invention is that withdrawing the expandable members by the application of a pulling force on the proximal elongate wire flexible wire urges the expandable members to assume a smaller expanded diameter while being withdrawn from the patient, thus decreasing the likelihood of injury to the vessel wall. Another advantage is that the cell patterns permit the expandable members to be retracted into the lumen of the delivery catheter after they have been partially or fully deployed. As such, if at any given time it is determined that the expandable member has been partially or fully deployed at an improper location, it may be retracted into the distal end of the delivery catheter and repositioned to the correct location.

Figure 14:
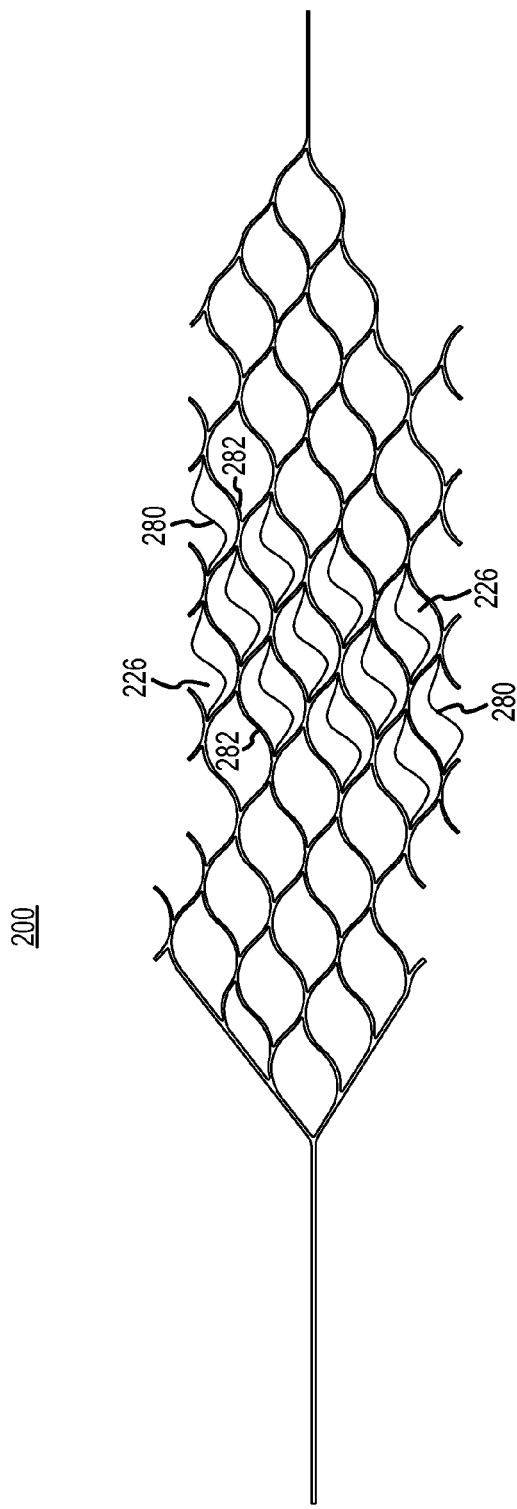
FIG. 14 illustrates a two-dimensional plane view of an expandable member of an embolic obstruction retrieval device in another embodiment.
Figure 15:
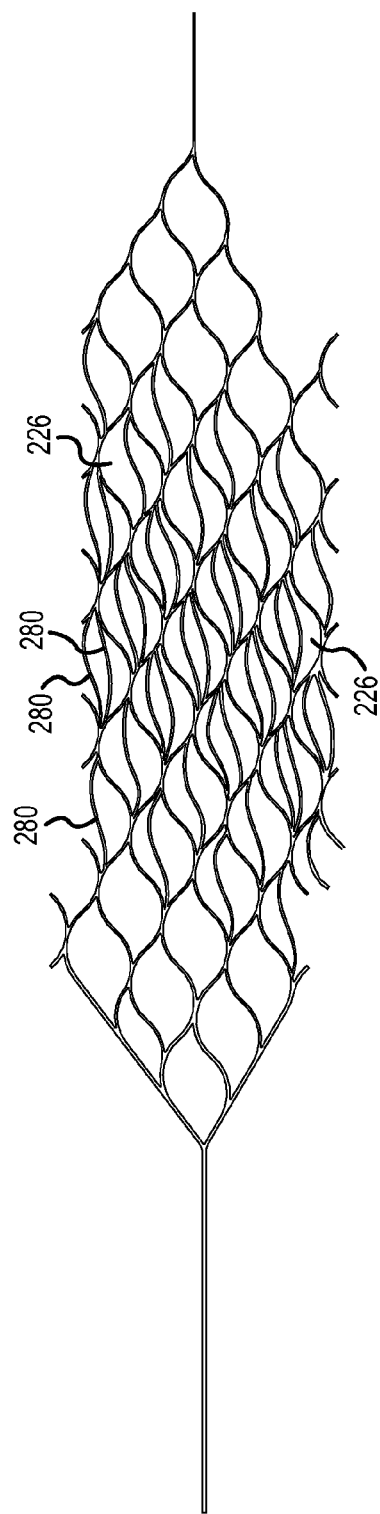
FIG. 15 illustrates a two-dimensional plane view of an expandable member of an embolic obstruction retrieval device in yet embodiment.

With reference to FIG. 14, a modified version of the retrieval device 200 of FIG. 6A is shown that includes thin strut elements 280 intersecting at least some of the cell structures 226 located in the cylindrical main body portion 216 of expandable member 212. The thin strut elements 280 are dimensioned to have a width of less than the strut elements 282 that form the cell structures 226. In alternative exemplary embodiments, strut elements 280 have an as-cut or polished width dimension that is between about 25% to about 50% smaller than the respective as-cut or polished width dimension of struts 262. The purpose of the thin struts 280 is to enhance the expandable member's ability to engage with and capture an embolic obstruction. This is accomplished by virtue of several factors. First, the thinner width dimensions of the struts 280 make it easier for the struts to penetrate the obstruction. Second, they act to pinch portions of the entrapped obstruction against the outer and wider strut elements 282 as the expandable member is deployed within the obstruction. Third, they may be used to locally enhance radial forces acting on the obstruction. It is important to note that the use of thin strut elements 280 is not limited to use within cell structures 226 that reside within the cylindrical main body portion 216 of the expandable member 212. They may be strategically positioned in any or all of the cell structures of the expandable member. Moreover, it is important to note that the use of thin strut elements 280 is not limited to the embodiment of FIG. 6, but are applicable to all the various embodiments disclosed herein. Lastly, in alternative exemplary embodiments, as shown in FIG. 15, multiple thin strut elements 280 are provided within one or more of the cell structures 226, and may also be used in conjunction with cell structures that have a single thin strut element and/or cell structures altogether devoid of thin strut elements.

Figure 16:
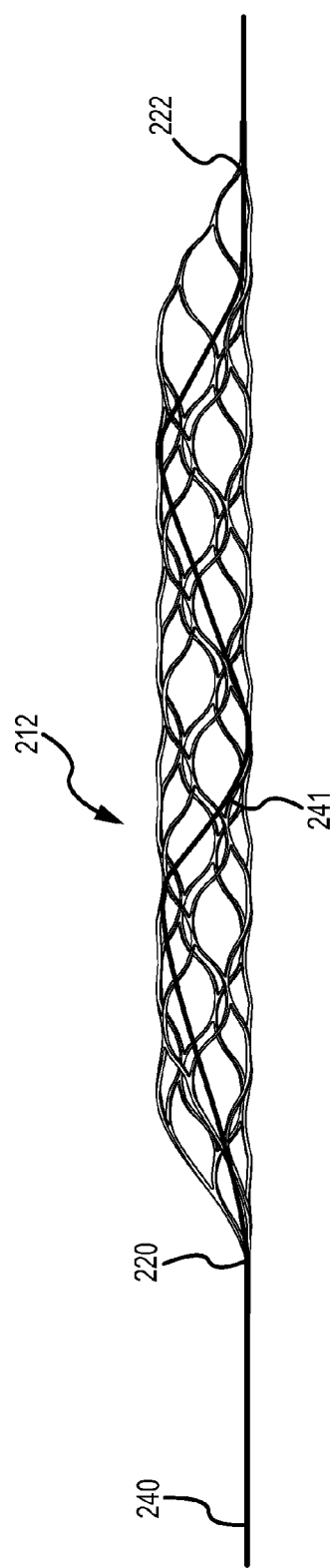
FIG. 16 illustrates an isometric view of an expandable member in another embodiment having an internal wire segment.

With continued reference to the embodiment of FIGS. 6A and 6B, the pushability of the expandable member 212 during its advancement to the treatment site of a patient may be enhanced by the inclusion of an internal wire segment 241 that extend between the proximal end 220 and distal end 222 of the expandable member 212. In this manner, the pushing force applied by elongate wire 240 is transmitted to both the proximal and distal ends of expandable device. The internal wire segment may be a discrete element that is attached to the proximal and distal ends of the expandable member, or may preferably be a co-extension of the elongate flexible wire 240. During delivery of the expandable member 212 to the treatment site in its compressed state, the internal wire segment 241 assumes a substantially straight or linear configuration so as to adequately distribute at least a part of the pushing force to the distal end 222 of the expandable member. When the expandable member 212 expands, it tends to foreshorten causing slack in the internal wire segment 241 that forms a long-pitched helix within the expandable member as shown in FIG. 16. An additional advantage associated with the use the internal wire segment 241 is that the formation of the internal helix upon expansion of the expandable member 212 may assist in capturing the embolic obstruction.

Figure 17:
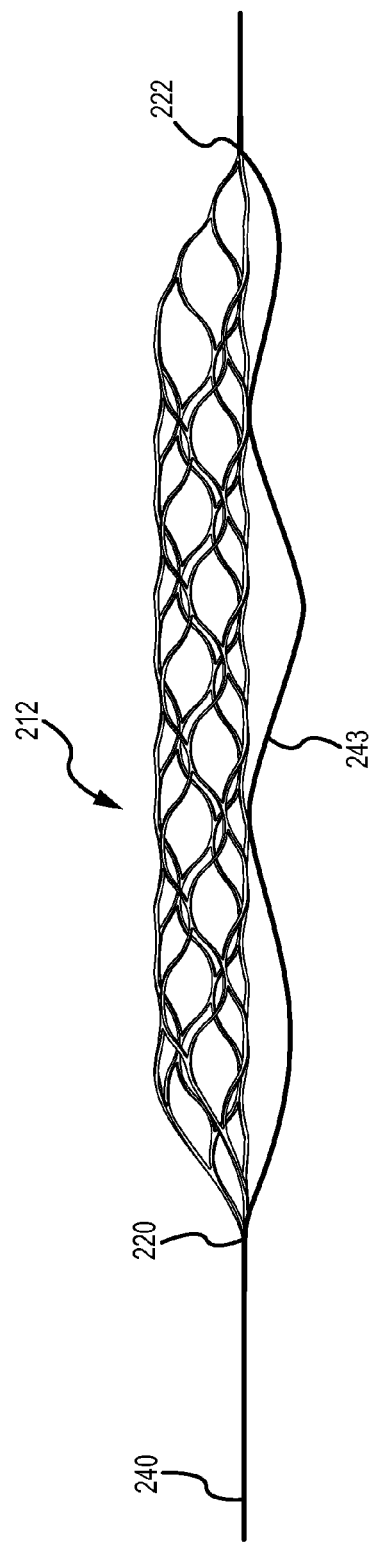
FIG. 17 illustrates an isometric view of an expandable member in another embodiment having an external wire segment.

In an alternative embodiment, the pushability of the expandable member 212 during its advancement to the treatment site of a patient may be enhanced by the inclusion of an external wire segment 243 that extend between the proximal end 220 and distal end 222 of the expandable member 212. In this manner, the pushing force applied by the elongate wire 240 is transmitted to both the proximal and distal ends of the expandable device. The external wire segment may be discrete element that is attached to the proximal and distal ends of the expandable member, or may preferably be a co-extension of the elongate flexible wire 240. During delivery of the expandable member 212 to the treatment site in its compressed state, the external wire segment 243 assumes a substantially straight or linear configuration so as to adequately distribute at least a part of the pushing force to the distal end 222 of the expandable member. When the expandable member 212 expands, it tends to foreshorten causing slack in the external wire segment 243 as shown in FIG. 17. An additional advantage associated with the use of the external wire segment 243 is that it directly acts on the obstruction while the expandable member 212 is expanded to assist in engaging and capturing the embolic obstruction.

Figure 18:
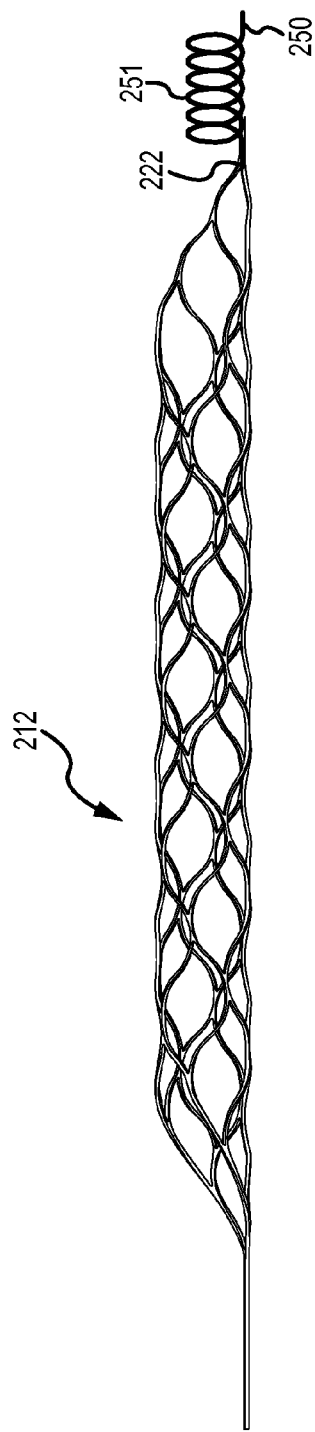
FIG. 18 illustrates an isometric view of an expandable member in yet another embodiment having a distal emboli capture device.

In yet another embodiment, a distal emboli capture device 251 is disposed on the distal wire segment 250, or otherwise attached to the distal end 222, of expandable member 212 as shown in FIG. 18. The function of the distal emboli capture device 251 is to capture emboli that may be dislodged from the embolic obstruction during the expansion of the expandable member 212 or during its removal from the patient to prevent distal embolization. In FIG. 18, the distal emboli capture device is shown as a coil. In alternative embodiments, baskets, embolic filters or other known emboli capture devices may be attached to the distal end 222 or distal wire segment 250 of expandable member 12.

Again, as with the embodiments of FIGS. 14 and 15, it is important to note that the features described in conjunction with FIGS. 16, 17 and 18 are not limited to the embodiment of FIG. 6, but are applicable to all the various embodiments disclosed herein.

While the above description contains many specifics, those specifics should not be construed as limitations on the scope of the disclosure, but merely as exemplifications of preferred embodiments thereof. For example, dimensions other than those listed above are contemplated. For example, retrieval devices having expanded diameters of any where between 1.0 and 100.0 millimeters and lengths of up to 5.0 to 10.0 centimeters are contemplated. Moreover, it is appreciated that many of the features disclosed herein are interchangeable among the various embodiments. Those skilled in the art will envision many other possible variations that are within the scope and spirit of the disclosure. Further, it is to be appreciated that the delivery of a retrieval device of the embodiments disclosed herein is achievable with the use of a catheter, a sheath or any other device that is capable of carrying the device with the expandable member in a compressed state to the treatment site and which permits the subsequent deployment of the expandable member within an embolic obstruction.

What is claimed is:

1. An embolic obstruction retrieval device comprising:
an elongate self-expandable member expandable from a first delivery position to a second placement position, in the first delivery position the expandable member being in an unexpanded position and having a nominal first diameter and in the second position the expandable member being in a radially expanded position and having a second nominal diameter greater than the first nominal diameter, the expandable member comprising a plurality of generally longitudinal undulating elements with adjacent undulating elements being interconnected in a manner to form a plurality of diagonally disposed cell structures, the expandable member having a proximal end portion with a first length and an elongate cylindrical main body portion with a second length, the elongate cylindrical main body portion located distal to the proximal end portion, the elongate cylindrical main body portion comprising at least a first circumferential row of cell structures that extends diagonally and circumferentially around a longitudinal axis of the expandable member, a second circumferential row of cell structures located distal to and interconnected with the first circumferential row of cell structures that extends diagonally and circumferentially around the longitudinal axis of the expandable member, a third circumferential row of cell structures located distal to and interconnected with the second circumferential row of cell structures that extends diagonally and circumferentially around the longitudinal axis of the expandable member, a fourth circumferential row of cell structures located distal to and interconnected with the third circumferential row of cell structures that extends diagonally and circumferentially around the longitudinal axis of the expandable member, the proximal end portion comprising multiple rows of cell structures with none of the multiple rows of cell structures extending circumferentially around the longitudinal axis of the expandable member, the second length of the elongate cylindrical main body portion being between 2.5 and 3.5 times greater than the first length of the proximal end portion, the outer-most cell structures in the proximal end portion having proximal-most wall segments that form first and second rail segments that each extend from a position at or near a proximal-most end of the expandable member to a position at or near a proximal end of the cylindrical main body portion, when the expandable member is cut and laid flat on a surface at least the first rail segment is substantially straight; and
a first proximally extending elongate flexible wire connected to the proximal-most end of the expandable member.

2. The embolic obstruction retrieval device of claim 1, wherein the first and second rail segments are of the same length.

3. The embolic obstruction retrieval device of claim 1, wherein in the radially expanded position the cylindrical main body portion comprises a first region and a second region, the second region having a diameter greater than the first region.

4. The embolic obstruction retrieval device of claim 3, wherein the diameter of the second region is between about 25.0 to about 35.0 percent greater than the diameter of the first region.

5. The embolic obstruction retrieval device of claim 3, wherein the second region is located distal to the first region.

6. The embolic obstruction retrieval device of claim 3, wherein the second region is located at a distal end of the cylindrical main body portion.

7. The embolic obstruction retrieval device of claim 1, wherein at least a portion of the expandable member is coated with a radiopaque material.

8. The embolic obstruction retrieval device of claim 1, further comprising radiopaque markers positioned at or near the proximal-most and distal-most ends of the expandable member.

9. The embolic obstruction retrieval device of claim 1, wherein each of the cell structures in the proximal end portion are larger than the cell structures in the elongate cylindrical main body portion.

* * * * *